(12) United States Patent
Mendoza et al.

(10) Patent No.: US 12,168,225 B2
(45) Date of Patent: Dec. 17, 2024

(54) SAMPLE COLLECTION AND DISPENSING DEVICE

(71) Applicant: SRI International, Menlo Park, CA (US)

(72) Inventors: Estevan Mendoza, Mountain View, CA (US); Eric Warner, Oceanside, CA (US)

(73) Assignee: SRI International, Menlo Park, CA (US)

( * ) Notice: Subject to any disclaimer, the term of this patent is extended or adjusted under 35 U.S.C. 154(b) by 817 days.

(21) Appl. No.: 17/295,195

(22) PCT Filed: Aug. 21, 2019

(86) PCT No.: PCT/US2019/047538
§ 371 (c)(1),
(2) Date: May 19, 2021

(87) PCT Pub. No.: WO2020/106345
PCT Pub. Date: May 28, 2020

(65) Prior Publication Data
US 2022/0016617 A1 Jan. 20, 2022

Related U.S. Application Data

(60) Provisional application No. 62/770,633, filed on Nov. 21, 2018.

(51) Int. Cl.
*B01L 3/00* (2006.01)
*B01L 3/02* (2006.01)
*G01N 1/14* (2006.01)

(52) U.S. Cl.
CPC ............. *B01L 3/022* (2013.01); *B01L 3/502* (2013.01); *G01N 1/14* (2013.01);
(Continued)

(58) Field of Classification Search
CPC .... B01L 3/022; B01L 3/502; B01L 2200/026; B01L 2200/0684; B01L 2200/16;
(Continued)

(56) References Cited

U.S. PATENT DOCUMENTS

4,468,044 A * 8/1984 Ulmer ................ F16J 15/123
277/596
9,442,046 B2 * 9/2016 Biadillah ........... A61B 10/0096
(Continued)

*Primary Examiner* — Jill A Warden
*Assistant Examiner* — Michael Stanley Gzybowski
(74) *Attorney, Agent, or Firm* — Dicke, Billig & Czaja, PLLC (57) ABSTRACT

Embodiments in accordance with the present disclosure are directed to sample collecting and dispensing methods and apparatuses. An example apparatus includes a capillary sampler disposed on a device first end, wherein the capillary sampler is configured to collect a fluid sample via an opening and a capillary body. The apparatus further includes a reagents chamber in fluid communication with the capillary sampler, and a barrier assembly disposed between the capillary sampler and the reagents chamber, wherein the barrier assembly is configured to separate fluid in the reagents chamber from the capillary sampler. A plunger assembly disposed on a device second end opposite the device first end, may modify the barrier assembly to dispense the fluid from the reagents chamber to the capillary sampler responsive to application of a force in the direction of the device first end.

16 Claims, 7 Drawing Sheets

(52) U.S. Cl.
CPC . *B01L 2200/026* (2013.01); *B01L 2200/0684* (2013.01); *B01L 2200/16* (2013.01); *B01L 2300/044* (2013.01); *B01L 2300/048* (2013.01); *B01L 2300/0838* (2013.01); *B01L 2300/123* (2013.01); *B01L 2300/14* (2013.01); *B01L 2300/161* (2013.01); *B01L 2400/0406* (2013.01); *B01L 2400/0487* (2013.01); *G01N 2001/149* (2013.01)

(58) Field of Classification Search
CPC ......... B01L 2300/044; B01L 2300/048; B01L 2300/0838; B01L 2300/123; B01L 2300/14; B01L 2300/161; B01L 2400/0406; B01L 2400/0487; G01N 1/14; G01N 2001/149

See application file for complete search history.

(56) References Cited

U.S. PATENT DOCUMENTS

| | | | |
|---|---|---|---|
| 2009/0215159 A1* | 8/2009 | Kirby | B01L 3/502 435/287.7 |
| 2011/0020195 A1 | 1/2011 | Luotola | |
| 2015/0343148 A1 | 12/2015 | Marmey | |
| 2018/0036725 A1 | 2/2018 | Le et al. | |
| 2018/0207638 A1* | 7/2018 | McNeely | B01L 3/5023 |
| 2018/0220945 A1 | 8/2018 | Sink et al. | |

\* cited by examiner

SAMPLE COLLECTION AND DISPENSING DEVICE

INCORPORATION BY REFERENCE

This Utility Patent Application claims priority under 35 U.S.C. § 371 to International Application Serial No. PCT/US2019/047538, filed Aug. 21, 2019, which claims the benefit of Provisional Patent Application No. 62/770,633, filed Nov. 21, 2018; which are both incorporated herein by reference in their entirety.

FEDERALLY-SPONSORED RESEARCH AND DEVELOPMENT

This invention was made with Government support under HHSO100201000007C awarded by Biomedical Advanced Research and Development Authority, Department of Health and Human Services. The government has certain rights in the invention.

OVERVIEW

This present application relates to handheld sample collection devices, in particular where the samples are biological fluids such as blood. In point-of-care systems for analyzing blood and other biologic samples, the samples are usually drawn from a skin prick. In many instances, it may be necessary for a technician to transfer the sample to a different receptacle and mix the sample with an aliquot of reagent prior to analysis. These extra steps can lead to inaccurate test results especially when a technician is processing many such samples at once. In addition, having to transfer a sample to a second receptacle before it can be loaded onto a corresponding testing device can lead to loss of a portion of the sample. In some cases, a biological sample may be stored in a buffer or other media prior to analysis, which may result in the measurement of the reagent, mixing of the reagent with the sample, and subsequent transfer of the final sample into a storage vessel or transfer of the sample to a storage vessel followed by addition of a reagent or reagents. In either case, the technician is tasked with additional steps to prepare the sample.

SUMMARY OF THE DISCLOSURE

Described herein are examples of sample collecting and dispensing devices. While sample collecting and dispensing devices were conceived of for taking up biological samples and subsequent testing of these biological samples, it is also conceivable to use the sample collecting and dispensing device for applying non-biological samples onto corresponding test devices, such as may be implemented for testing for illegal substances, among other non-limiting examples. Examples of the present disclosure allow for a biological sample, such as blood, to be taken up and stored for subsequent analysis. In some examples of the device, a pre-defined amount of biological sample can be taken up and mixed with a pre-measured amount of liquid. Eliminating the additional processing step(s) may therefore decrease the time and amount of error in processing samples, especially when processing a large number of samples.

Various examples of the present disclosure are directed toward a sample collecting and dispensing apparatus. Such example apparatus includes a capillary sampler disposed on a device first end, wherein the capillary sampler is configured to collect a fluid sample via an opening and a capillary body. A reagents chamber is in fluid communication with the capillary sampler, and a barrier assembly is disposed between the capillary sampler and the reagents chamber. The barrier assembly is configured to separate fluid in the reagents chamber from the capillary sampler. Additionally, a plunger assembly disposed on a device second end opposite the device first end is configured to modify the barrier assembly to dispense the fluid from the reagents chamber to the capillary sampler responsive to application of a force in the direction of the device first end.

In additional example embodiments, the capillary sampler is configured to collect and dispense a fluid sample via an opening and a capillary body. For instance, the reagents chamber may store a fluid reagent specific to the fluid sample to be collected. The reagents chamber includes a reagents chamber distal end attached to and in fluid communication with the capillary sampler and a reagents chamber proximal end. A liquid barrier disposed on the reagents chamber distal end is configured to prevent the fluid reagent from passing from the reagents chamber to the capillary sampler under atmospheric pressures, and a plunger assembly including a handle and a plunger rod is disposed on a device second end. The plunger assembly is adjacently connected to the reagents chamber proximal end through mated threads, and the plunger rod is configured to translate distally along the reagents chamber to decrease a volume of the fluid reagent in the reagents chamber and permit the fluid reagent to release from the reagents chamber.

In various example embodiments, a method of sample collection and dispensing includes collecting a fluid sample by capillary force through an opening in a capillary sampler disposed on a first end of a sample collection and dispensing apparatus. A volume of the fluid sample is limited by a barrier assembly disposed within the capillary sampler. The sample collection and dispensing apparatus are coupled to a receiving port of a corresponding testing apparatus. Responsive to application of a force on a plunger assembly disposed on a second end of the sample collection and dispensing apparatus opposite the first end of the sample collection and dispensing apparatus, the barrier assembly is modified to dispense fluid from a reagents chamber in fluid communication with the capillary sampler. The fluid from the reagents chamber and the fluid sample from an opening in a capillary sampler are thereby dispensed.

In further example embodiments, a sample collecting and dispensing apparatus includes a housing having a proximal end and a distal end, a capillary sampling tip, a flow barrier, and a plunger. The housing defines a reagent chamber in the sample collecting and dispensing apparatus, and the capillary sampling tip is disposed at the distal end of the housing. The capillary sampling tip has a tubular body that defines and surrounds a capillary passage along the length of the capillary sampling tip. The capillary passage may be in selective fluid communication with the reagent chamber at a proximal portion of the capillary sampling tip, and the capillary passage may terminate at a distal opening of the capillary sampling tip. The flow barrier may be disposed between the capillary passage and the reagent chamber, and the flow barrier may prevent the flow of liquid from the reagent chamber to the capillary passage. The plunger may be at least partially disposed within a proximal portion of the housing. Moreover, the plunger may be displaceable along the reagent chamber. Advancement of the plunger along a distal direction with respect to the housing may apply pressure to the flow barrier by way of liquid reagent disposed in the reagent chamber displacing at least a portion of the flow barrier to permit reagent to flow from the reagent chamber to the capillary sampling tip.

In some examples, the porous venting barrier includes sintered polymeric material. Additionally, the sample collecting and dispensing apparatus may include a porous venting barrier disposed in the capillary sampling tip along the capillary passage. The porous venting barrier may permit the passage of gaseous fluid therethrough but substantially prohibiting the passage of liquid fluid therethrough. In such examples, the capillary sampling tip may define at least one vent passage through the tubular body of the capillary sampling tip to place a portion of the capillary passage in direct fluid communication with an outer surface of the capillary sampling tip, and the at least one vent passage may be located proximally with respect to the porous venting barrier. Similarly, the porous venting barrier may permit gas in the capillary passage distal to the porous venting barrier to exit by way of the at least one vent passage in response to liquid entering the capillary passage by way of the distal opening. Moreover, an internal surface of the capillary passage may be coated with a hydrophilic material.

In some examples, wherein the flow barrier includes a liquid barrier configured to maintain the fluid in the reagents chamber in response to pressure within the reagents chamber being below a threshold level of pressure, and permit passage of fluid from the reagents chamber to the capillary sampler in response to pressure within the reagents chamber being at or above the threshold level of pressure. Moreover, the flow barrier may include a frangible layer of material configured to be ruptured when a threshold differential pressure across the frangible layer of material is exceeded. Additionally and/or alternatively, the flow barrier may include a displaceable plug that is dislodged when a threshold differential pressure across the displaceable plug is exceeded. For instance, the displaceable plug may be configured to rest on the porous venting barrier and may be sized to permit fluid flow between the displaceable plug and an inner wall surface of the capillary passage when the displaceable plug is in physical contact with the porous venting barrier. In some example embodiments, the flow barrier includes an elastomeric cord.

In accordance with various embodiments, the sample collecting and dispensing apparatus further includes at least one boss on an exterior surface configured to facilitate a mechanical interlock between the sample collecting and dispensing apparatus and a port of a corresponding test device. Additionally, the sample collecting and dispensing apparatus may include a handle coupled to at least one of the plunger and the housing. The handle may be coupled to the housing by way of a helical thread that causes the handle to be advanced distally with respect to the housing when the handle is rotated with respect to the housing. Additionally and/or alternatively, the helical thread may be disposed along an outer surface of the housing, and the helical thread may mate with at least one guide boss disposed inside a bore of the handle. Moreover, the helical thread may be disposed along an inner bore of the handle, and the helical thread may mate with at least one guide boss disposed on an outer surface of the housing. In some examples, the handle is configured to provide a visual indication in response to a volume of the fluid reagent in the reagent chamber being fully dispensed.

As a specific example, a method of sample collection and dispensing in accordance with the present disclosure may include collecting a fluid sample by capillary action through an opening defined at a distal end of a capillary sampler disposed on a distal end of a sample collection and dispensing apparatus, coupling the sample collection and dispensing apparatus to a receiving port of a corresponding testing apparatus, and responsive to application of a force on a plunger assembly disposed on a proximal end of the sample collection and dispensing apparatus, removing a liquid flow barrier within the sample collection and dispensing apparatus to dispense a mixture of reagent and the fluid sample by way of the opening at the distal end of the capillary sampler into the testing apparatus. In such examples, the volume of the fluid sample may be limited by a porous venting barrier disposed within the capillary sampler. Additionally, the flow barrier may include a displaceable plug that is displaced in response to a differential pressure across the displaceable plug exceeding a threshold value. Moreover, the flow barrier may include a frangible membrane that is ruptured in response to a differential pressure across the frangible membrane exceeding a threshold value.

BRIEF DESCRIPTION OF THE DRAWINGS

Various example embodiments may be more completely understood in consideration of the following detailed description in connection with the accompanying drawings, in which.

While various embodiments discussed herein are amenable to modifications and alternative forms, aspects thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DETAILED DESCRIPTION

Aspects of the present disclosure are believed to be applicable to a variety of apparatuses and methods involving sample collection and dispensing. In certain implementations, a sample collecting and dispensing apparatus includes a capillary sampler disposed on a device first end. The capillary sampler is configured to collect a fluid sample via an opening and a capillary body. The sample collecting and dispensing apparatus further includes a reagents chamber in fluid communication with the capillary sampler, and a barrier assembly disposed between the capillary sampler and the reagents chamber. The barrier assembly is configured to separate fluid in the reagents chamber from the capillary sampler. Moreover, the sample collecting and dispensing apparatus includes a plunger assembly disposed on a device second end opposite the device first end. The plunger assembly is configured to modify the barrier assembly to dispense the fluid from the reagents chamber to the capillary sampler responsive to application of a force in the direction of the device first end. While the present invention is not necessarily limited to such applications, various aspects of the invention may be appreciated through a discussion of various examples using this context.

Accordingly, in the following description various specific details are set forth to describe specific examples presented herein. It should be apparent to one skilled in the art, however, that one or more other examples and/or variations of these examples may be practiced without all the specific details given below. In other instances, well known features have not been described in detail so as not to obscure the description of the examples herein. For ease of illustration, the same reference numerals may be used in different diagrams to refer to the same elements or additional instances of the same element.

Various embodiments in accordance with the present disclosure are directed to a method and apparatus for sample collecting and dispensing. As previously described, the sample collecting and dispensing apparatus may include a capillary sampler, a reagents chamber, a barrier assembly, and a plunger assembly. In various examples, the capillary sampler is disposed on a device first end, and configured to collect a fluid sample via an opening and a capillary body. The reagents chamber is in fluid communication with the capillary sampler, and a barrier assembly is disposed between the capillary sampler and the reagents chamber. The barrier assembly is configured to separate fluid in the reagents chamber from the capillary sampler. The plunger assembly is disposed on a device second end opposite the device first end. The plunger assembly is configured to modify the barrier assembly to dispense the fluid from the reagents chamber to the capillary sampler responsive to application of a force in the direction of the device first end.

According to additional example embodiments, a sample collecting and dispensing apparatus includes a housing having a proximal end and a distal end, the housing defining a reagent chamber. A capillary sampling tip may be disposed at the distal end of the housing, where the capillary sampling tip has a tubular body that defines and surrounds a capillary passage along the length of the capillary sampling tip. The capillary passage may be in selective fluid communication with the reagent chamber at a proximal portion of the capillary sampling tip. The capillary passage may terminate at a distal opening of the capillary sampling tip.

In various examples, the barrier assembly further includes a venting barrier disposed in the capillary body and in a vent defined by a side wall of the capillary body. The venting barrier may be configured to limit a volume of the fluid sample collected in the capillary body in response to pressure within the reagents chamber being below a threshold level of pressure, and permit passage of fluid from the reagents chamber to the capillary sampler in response to pressure within the reagents chamber being at or above the threshold level of pressure, as described further herein. As such, the venting barrier may be configured to permit air to exit the capillary body via the vent in the side wall of the capillary body responsive to collection of the fluid sample via the opening. Various materials may be used in assembling the sample collecting and dispensing apparatus. For instance, an internal surface of the capillary body and an internal surface of the opening of the capillary sampler may coated with a hydrophilic material, and the venting barrier may include sintered polyethylene grains, among other non-limiting example materials.

The venting barrier may, in some examples, be a porous venting barrier. The porous venting barrier may be disposed in the capillary sampling tip along the capillary passage, the porous venting barrier permitting the passage of gaseous fluid there through but substantially prohibiting the passage of liquid fluid. In such examples, the capillary sampling tip defines at least one vent passage through the tubular body of the capillary sampling tip to place a portion of the capillary passage in direct fluid communication with an outer surface of the capillary sampling tip, the at least one vent passage being located proximally with respect to the porous venting barrier. The porous venting barrier may permit gas in the capillary passage distal to the porous venting barrier to exit by way of the at least one vent passage in response to liquid entering the capillary passage by way of the distal opening. Accordingly, in some examples, an internal surface of the capillary passage is coated with a hydrophilic material.

Additional configurations of a barrier assembly are contemplated. For instance, the barrier assembly may include a venting barrier disposed in the capillary body, and a liquid barrier including a ball configured to displace into a cavity of the capillary body in response to pressure within the reagents chamber being at or above a threshold level of pressure. In such examples, the venting barrier is configured to prevent the ball of the liquid barrier from passing beyond the cavity of the capillary body and to permit passage of the fluid from the reagents chamber into the capillary sampler. Additionally and/or alternatively, the barrier assembly may include a pedestal disposed in the capillary body and configured to prevent the ball of the liquid barrier from passing beyond a particular point within the capillary body and to permit passage of the fluid from the reagents chamber into the capillary sampler. The venting barrier, as shown in the examples, is cylindrical in shape but can be of any suitable shape.

Additionally, the sample collecting and dispensing apparatus includes a flow barrier disposed between and the capillary passage and the reagent chamber. The flow barrier may prevent the flow of liquid from the reagent chamber to the capillary passage. Additionally, a plunger may be at least partially disposed within a proximal portion of the housing. The plunger may be displaceable along the reagent chamber, where advancement of the plunger along a distal direction with respect to the housing applies pressure to the flow barrier by way of liquid reagent disposed in the reagent chamber to displace at least a portion of the flow barrier to permit reagent to flow from the reagent chamber to the capillary sampling tip. The flow barrier includes a liquid barrier configured to maintain the fluid in the reagents chamber in response to pressure within the reagents chamber being below a threshold level of pressure, and permit passage of fluid from the reagents chamber to the capillary sampler in response to pressure within the reagents chamber being at or above the threshold level of pressure. For instance, the flow barrier may include a frangible layer of material configured to be ruptured when a threshold differential pressure across the frangible layer of material is exceeded. Additionally and/or alternatively, the flow barrier may include a displaceable plug that is dislodged when a threshold differential pressure across the displaceable plug is exceeded. In such examples, the displaceable plug is configured to rest on the porous venting barrier and is sized to permit fluid flow between the displaceable plug and an inner wall surface of the capillary passage when the displaceable plug is in physical contact with the porous venting barrier. In various embodiments, the flow barrier includes an elastomeric cord.

The flow barrier may be disposed on the reagents chamber distal end configured to maintain liquid within the reagents chamber and prevent any liquid from passing from the reagents chamber to the capillary sampler under atmospheric pressures, but when the pressure within the reagents chamber is increased (such as when the physical internal volume of the reagents chamber is decreased but the liquids volume remains the same), the flow barrier will be breached allowing the liquid maintained within the reagents chamber to be released. In some examples, the flow barrier is a deformable plug. In some examples, the flow barrier is a deformable plug made from an elastomeric material. In yet other examples, the flow barrier is a short stretch of elastomeric cord.

The sample collecting and dispensing apparatus may also include at least one boss on an exterior surface, configured to facilitate a mechanical interlock between the sample collecting and dispensing apparatus and a port of a corresponding test device. For instance, the sample collecting and dispensing apparatus may include a handle coupled to at least one of the plunger and the housing. The handle may be coupled to the housing by way of a helical thread that causes the handle to be advanced distally with respect to the housing when the handle is rotated with respect to the housing. The helical thread may be disposed along an outer surface of the housing, and the helical thread mates with at least one guide boss disposed inside a bore of the handle. Additionally and/or alternatively, the helical thread is disposed along an inner bore of the handle, and the helical thread mates with at least one guide boss disposed on an outer surface of the housing. In some examples, the handle is configured to provide a visual indication in response to a volume of the fluid reagent in the reagent chamber being fully dispensed. The handle may allow a user easier grip of the device when taking up sample and subsequently attaching it to a test device and dispensing the liquid and sample onto the test device. The sample collecting and dispensing device may include coupling features disposed on the exterior of the device for coupling the device to a corresponding test device. The sample collecting and dispensing device may also include external winged-grips that aid a user in installing the device into a corresponding test device. In some examples of the sample collecting and dispensing device, a handle may be attached to the plunger assembly for easier actuation of the device. In some examples of the sample collecting and dispensing device, coupling features are disposed on the exterior of the device for coupling the device to a corresponding test device. This prevents accidental or mis-delivery of sample onto the test device. In some examples, the mating threads, e.g., coupling features, are configured to lock in a fixed position responsive to coupling of the apparatus to the corresponding test device.

The sample collecting and dispensing device also includes a reagents chamber. The reagents chamber may store a fluid reagent specific to the fluid sample to be collected. The reagents chamber may include a reagents chamber distal end attached to and in fluid communication with the capillary sampler and a reagents chamber proximal end. In some examples, the reagents chamber can hold approximately 100 µL to approximately 1000 µL of liquid. In other examples, the reagents chamber can hold approximately 250 µL to approximately 750 µL of liquid. The reagents chamber distal end is attached to and in fluid communication with the capillary sampler.

Finally, the sample collecting and dispensing device includes a plunger disposed in a device second end and adjacently connected to the reagents chamber proximal end configured to maintain any liquid within the reagents chamber by acting as a seal at the reagents chamber proximal end and configured to break the flow barrier when pushed in the direction of the device first end. The plunger may include a plunger rod attached to a plunger piston, where the plunger piston acts as a barrier against liquid escaping the reagents chamber. In some examples, the plunger piston and the internal surface of the reagents chamber includes mated threads that allow a user to rotate the plunger thereby decreasing the reagents chamber overall volume when the plunger piston and plunger rod assembly is rotated and travels along the long axis of the sample collecting and dispensing device. The plunger, e.g., plunger assembly, may include a plunger rod and a plunger piston disposed a device second end and adjacently connected to the reagents chamber proximal end through mated threads disposed on the plunger piston surface and reagents chamber internal surface, wherein the plunger piston is configured to maintain any liquid within the reagents chamber by acting as a seal at the reagents chamber proximal end and wherein the plunger piston is configured to translate distally along the corresponding mated threads to decrease the overall volume of the reagents chamber to create pressures greater than atmospheric pressure, thereby dislodging the plug barrier and allowing any liquid to release from the reagents chamber.

Sample collection and dispensing using the aforementioned apparatus includes collecting a fluid sample by capillary action through an opening defined at a distal end of a capillary sampler disposed on a distal end of a sample collection and dispensing apparatus. A volume of the fluid sample may be limited by a porous venting barrier disposed within the capillary sampler, as described herein. The sample collection and dispensing apparatus may be coupled to a receiving port of a corresponding testing apparatus. Responsive to application of a force on a plunger assembly disposed on a proximal end of the sample collection and dispensing apparatus, a liquid flow barrier may be removed within the sample collection and dispensing apparatus to dispense a mixture of reagent and the fluid sample by way of the opening at the distal end of the capillary sampler into the testing apparatus. As described herein, the flow barrier may include a displaceable plug that is displaced in response to a differential pressure across the displaceable plug exceeding a threshold value. Additionally and/or alternatively, the flow barrier includes a frangible membrane that is ruptured in response to a differential pressure across the frangible membrane exceeding a threshold value.

Described herein are sample collecting and dispensing devices that are configured to draw up a sample and subsequently dispensed along with a diluting media such as a buffer or other reagent. The sample collection and dispensing device described herein are portable, handheld sample collection and dispensing devices that are able to take up an aliquot of sample via capillary action, and then either store the sample or mix the sample with a premeasured amount of reagent contained within the sample collection and dispensing device. The sample, either untreated or mixed with reagent then subsequently may be ran on an analysis device.

In general, the sample collection and dispensing device includes a handle, a plunger body, a plunger piston, a reagent chamber, a barrier separating the reagents from the rest of the sample collection and dispensing device, a venting barrier, and an open capillary tip.

Figure 1:
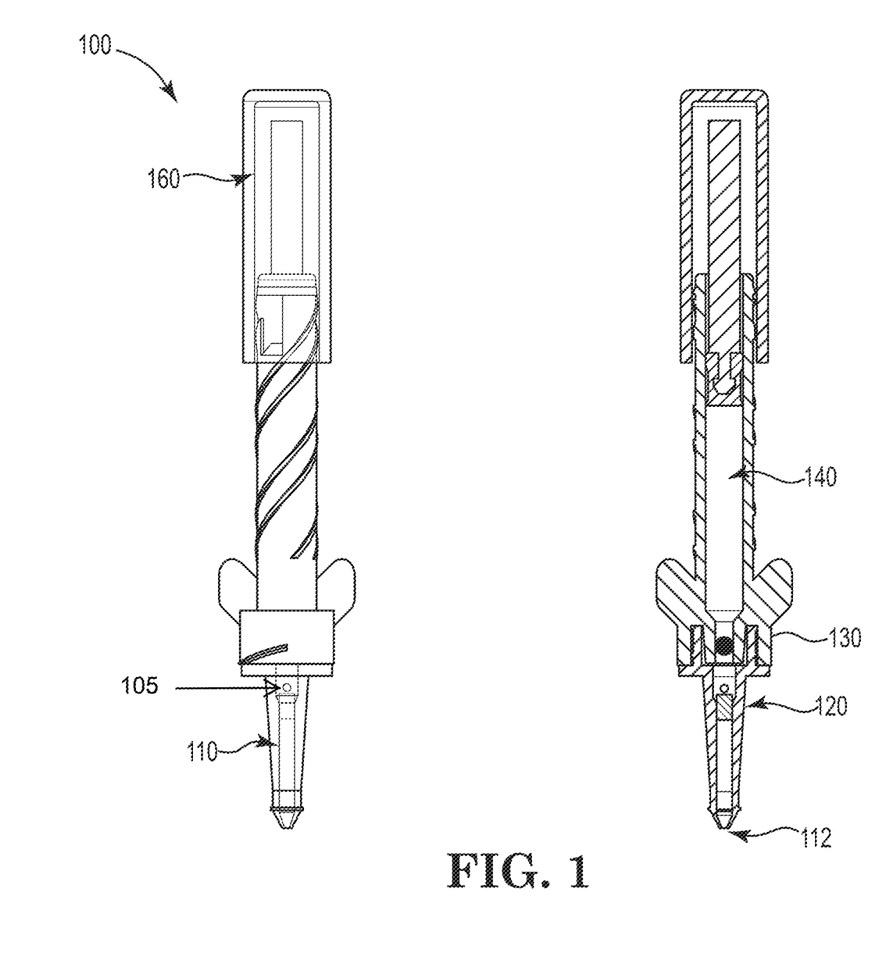
FIG. 1 illustrates an example of a sample collection and dispensing device, consistent with the present disclosure.
Figure 3A:
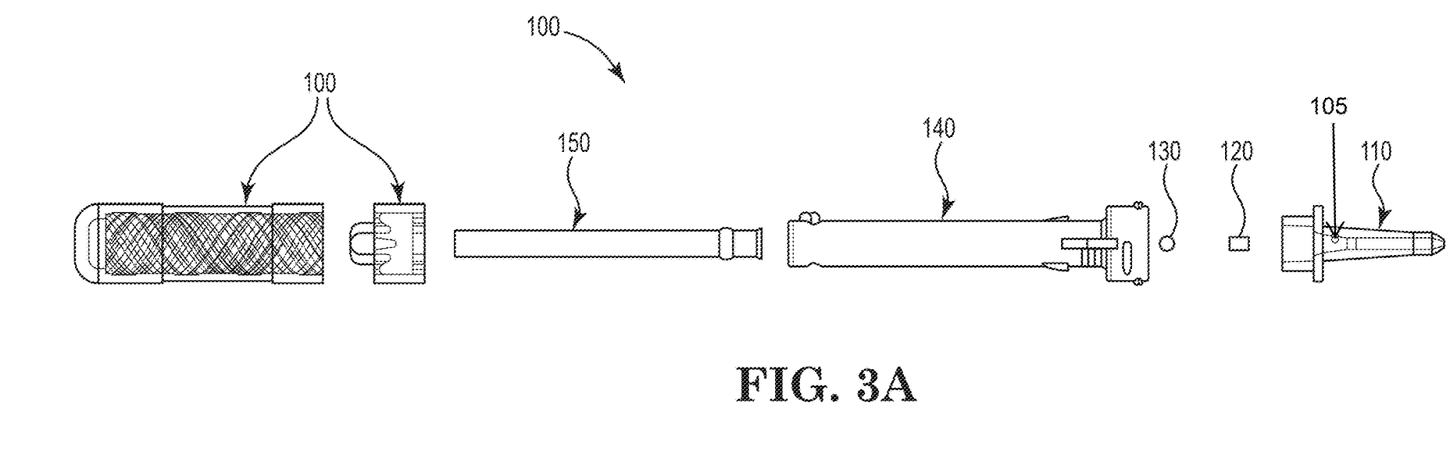
FIG. 3A illustrates an exploded view of an example sample collection and dispensing device, consistent with the present disclosure.
Figure 3B:
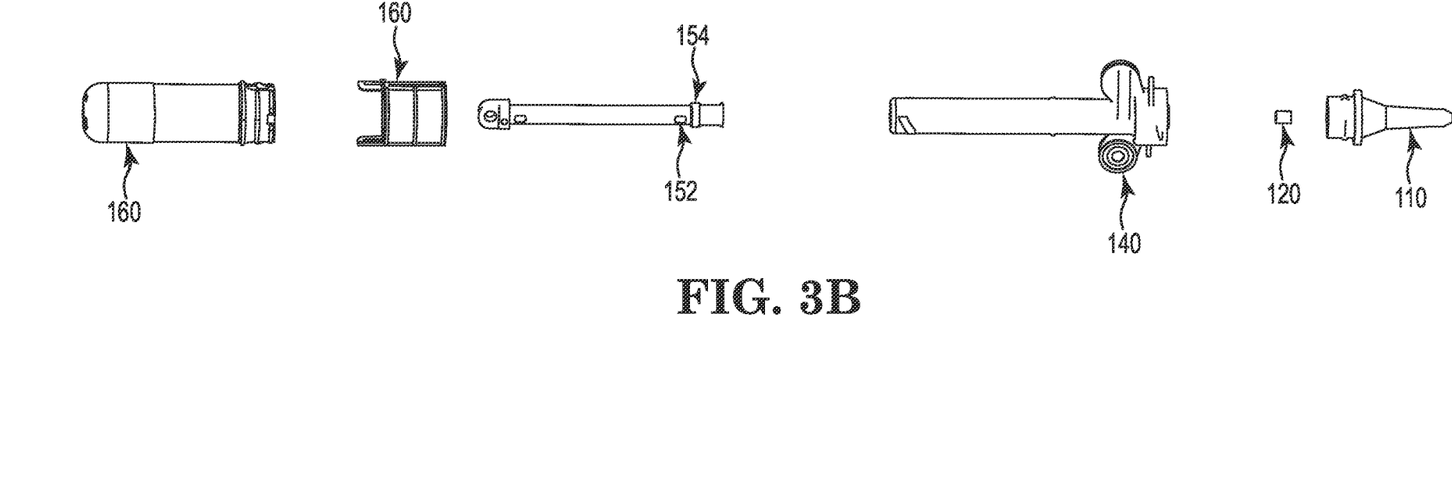
FIG. 3B illustrates an exploded view of an example sample collection and dispensing device with suggested measurements, consistent with the present disclosure.

FIG. 1 illustrates an example of a sample collection and dispensing device 100, consistent with the present disclosure. In general, device 100 includes a capillary sampler 110 disposed on the distal end, a venting barrier 120, a flow barrier 130, a reagents chamber 140, a plunger 150, and a handle assembly portion 160. FIG. 3A shows an exploded view of device 100.

In general, the capillary sampler 110 includes an opening 112 and a capillary body that extends the length of capillary sampler 110 which allows for fluid communication between capillary body and reagents chamber 140 when device 100 is in a position where a sample taken up by the capillary is mixed with the contents of reagents chamber 140. The capillary body is adjacent to and connected to the reagents chamber (e.g., housing) such that liquid can be pushed into the capillary body when the flow barrier is perturbed. In the example of processing blood, a subject may receive a finger prick and a small aliquot of blood may be extruded from the skin. A user then can hold the capillary tip up to the surface of the blood droplet to collect the sample. The sample will be taken up into the capillary portion of the capillary body and held there until applied to an analysis device. In general, approximately 15 to 50 microliters of sample may be held within the capillary. Further included in capillary sampler 110 is a venting aperture 105. Venting aperture allows air that was previously in the capillary body prior to uptake of a sample to be pushed out and displaced by the sample.

A capillary tip can be made to hold a maximum or minimum amount of sample. In some examples the capillary body can hold up to about 10 μL or about 50 μL of sample. In other examples, the capillary body can hold as little as 25-40 μL of sample. In some instances, the inside surface of the capillary body and opening can be coated with a hydrophobic compound so that sample will easily release from the capillary.

In general, the capillary sampler may also include external features that aide with its coupling to a corresponding test device. These external features may be mated protrusions with corresponding indentation in the test device. Other examples of external features may be threads that screw into the corresponding test device.

Staying with this embodiment, reagents chamber 140 is a hollow cylindrical tube with fittings on both ends. The reagent chamber distal end is coupled to the capillary body while the reagent chamber proximal end is coupled to the handle assembly portion. Reagents chamber 140 can be configured to have a known volume. In some examples, the reagent chamber can hold a known volume of liquids. It would be advantageous for the device to hold a requisite amount of reagent such that when a test sample is taken up, the sample can easily be introduced onto a test assay cartridge with the correct amount of reagent for diluting the sample without farther steps by a technician.

Contained within the coupling of the capillary sampler 110 to the reagent chamber 140 are the venting barrier 120 and the flow barrier 130. Prior to use, a space separates flow barrier 130 from venting barrier 120. When device 100 is installed, venting barrier 120 can be pressed into venting aperture 105 such that venting barrier 120 serves as a stop for the sample to ensure that a correct volume of sample is taken up. Venting barrier 120 may allow passage of air but prevents the passage of liquid from going through at atmospheric pressures. But at higher pressures, liquids may pass through the venting barrier. As a non-limiting example, the venting barrier can be made up of grains of polyethylene that have been sintered to give it rigidity. The venting barrier can be cut from a sheet into cylindrical shapes by using a coring tool. The venting barrier can also be directly sintered into the specified shape, thereby skipping the sheet cutting step mentioned earlier.

Flow barrier 130 may be configured to seal the liquids (e.g. reagents, buffers) contained within the reagents chamber 140 at atmospheric pressures. Flow barrier 130 may be configured to break or break away when a threshold amount of pressure is built up inside the reagents chamber 140. The pressure increase from atmospheric pressures can be anything greater than 15 psi, sufficient to perturb the flow barrier. In this first embodiment, flow barrier 130 is a malleable ball. In other non-limiting examples, the flow barrier may be a plug, where the plug can be a piece of cord or cylinder. In some embodiments, the plug can be made of an appropriate elastomeric material. In this example, the flow barrier is pressed into the opening of the reagents chamber and forms a seal with the distal end of reagents chamber 140, providing a hermetic seal for the liquids contained within the reagents chamber. In other embodiments, the flow barrier may be a membrane or heat seal foil that breaks under a threshold amount of pressure. For this embodiment of the assembled device, the flow barrier is fitted to the distal end opening of the reagents chamber.

In the embodiments of the device where the flow barrier is a deformable ball or plug, the ball or plug can be composed of an elastomeric material such as natural rubber. Non-limiting examples of suitable elastomeric materials are: unsaturated rubbers such as natural polyisoprene, synthetic polyisoprene, polybutadiene, chloroprenes, butyl rubbers, styrene-butadiene rubbers, nitrile rubbers, hydrogenated nitrile rubbers, saturated rubbers such as ethylene propylene rubbers, epichlorohydrin rubber, polyacrylic rubber, silicone rubber, fluorosilicone rubber, fluoroelastomers, perfluoroelastomers, polyether block amides, chlorosulfonated polyethylenes, ethylene vinyl acetates and so forth.

Figure 4A:
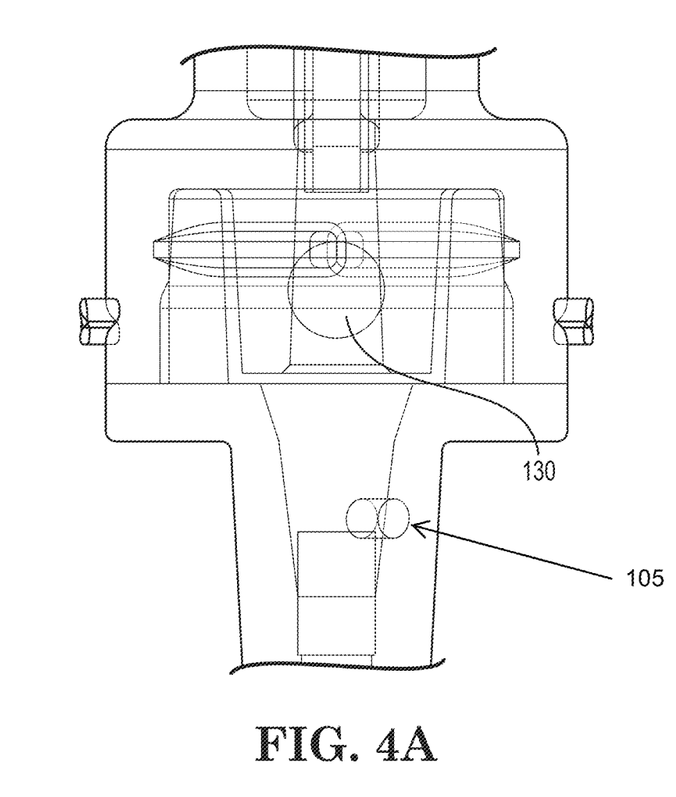
FIG. 4A illustrates an example sample collection and dispensing device including a flow barrier before the seal between the flow barrier and distal end of a reagents chamber being broken, consistent with the present disclosure.
Figure 4B:
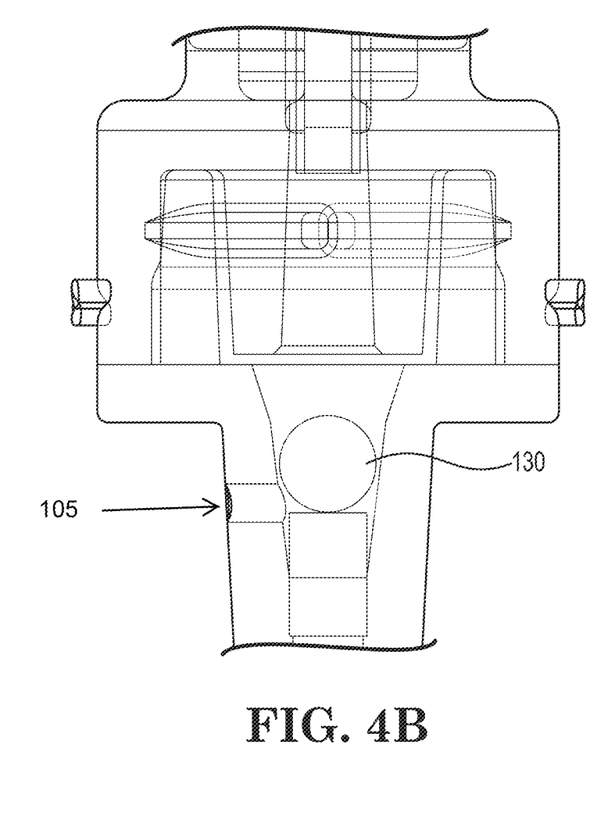
FIG. 4B illustrates an example sample collection and dispensing device including a flow barrier after it has been separated from the distal end of a reagents chamber, consistent with the present disclosure.

FIG. 4A illustrates an example sample collection and dispensing device including a flow barrier before the seal between the flow barrier and distal end of a reagents chamber being broken, consistent with the present disclosure. Particularly, FIGS. 4A and 4B are close up schematics depicting the position of the flow barrier prior to the sample collecting and dispensing device being used and after the flow barrier has been detached from the distal end of the reagents chamber. In this particular example, the flow barrier is a deformable ball that will be held up over the proximal end of the capillary sampler by the venting barrier and allow liquid to flow past. In other examples, the proximal end of the capillary sampler can have space or a cavity to retain the flow barrier once it has been separated from the distal end of the reagents chamber.

Plunger 150 can translate along the longitudinal axis of device 100. The distal end of the plunger is in fluid communication with reagents chamber 140. Plunger 150 is configured to prevent liquids contained within reagents chamber 140 from leaking past plunger 150 when actuated. In a first position, plunger 150 forms the proximal barrier of reagents chamber 140 and maintains the volume of liquids contained within reagents chamber 140, while flow barrier 130 provides the seal at reagents chamber 140 distal end for maintaining the liquids. In this first position, the capillary sampler is empty and yet to draw up a sample. In this first plunger position, the venting barrier is positioned to cover the venting aperture 105 such that no sample can be taken up through capillary action. Furthermore, in this first plunger position, the seal between the distal end of the reagents chamber and the flow barrier is also such that no liquid escapes from the reagents chamber.

Continuing with this first embodiment, device 100 has a handle 160. Handle 160 is mated with plunger 150. Handle 150 allows a user to easily grip device 100 and actuate plunger 150 along the long axis of device 100. In some instances, the handle can include screw-type threads with corresponding threads on plunger 150 such that when turned one direction followed by a push, handle 160 engages with plunger 150 and pushes plunger 150 towards the distal portion of the device breaking the seal between. In other examples, device 100 can include a handle having a screw-type thread for pushing the plunger distally, there may be haptic or auditory indicators (e.g. click or more than one click) that alerts the user that pushed the handle a proper distance and/or now to release the handle.

In some embodiments, a user can push on the handle to actuate the plunger distally. Plunger 150 can further include a plunger rod 152 and a plunger piston 154. Plunger 150 can be pushed into a retracted position where plunger 150 creates a pressure within reagents chamber 140. Several things occur when plunger 150 is actuated into this second position. For one, when the plunger is in this retracted position, when enough pressure builds up in the reagents chamber and the seal between the distal end of the reagents chamber and the flow barrier is broken.

When the seal between the distal end of the reagents chamber and the flow barrier is broken, this allows the liquid contained within the reagents chamber to flow toward the capillary sampler through its capillary and flushing the sample onto a corresponding analysis device. Also, for the device embodiment where the flow barrier is a ball, when plunger 150 is in this extended position, the seal between the distal end of the reagents chamber and the flow barrier become unsealed and any liquid contained within the reagents chamber is able to flow in the distal direction towards the capillary sampler. In the instance where the flow barrier is in the form of a deformable ball or the like, the flow barrier will fall away once enough pressure is applied and the seal between the distal end of the reagents chamber and the flow barrier is broken.

The venting barrier prevents the flow barrier from blocking liquid from flowing to the capillary sampler by acting as a platform or pedestal on which the flow barrier may sit if the flow barrier does not fall into the empty space surrounding the venting barrier. As previously mentioned, when the flow barrier is a ball or has a ball-like form, pulling the plunger in the proximal direction (away from the capillary sampler), release the seal between the distal end of the reagents chamber and the "ball-form" flow barrier allowing the liquid to flow past the flow barrier. In some instances, when seal is released/broken, the flow barrier can fall away into a cavity (not shown) located within the capillary sampler 110 thus allowing any liquid maintained within the reagents chamber to flow through the capillary sampler. Furthermore, as an extra precaution, venting barrier acts as a pedestal for the liquids barrier to prevent it from hindering liquid flow toward the capillary sampler. In the example where the flow barrier is ball-shaped, the venting barrier elevates the flow barrier so that the flow barrier does not seal the surface of the capillary bore of the capillary sampler so that liquid is not prevented from flowing from the reagents chamber to the capillary sampler. In other examples, the proximal end of the capillary sampler may include a pedestal or protrusion that is able to support the flow barrier during dispensing.

In other embodiments where the flow barrier is a perforable membrane, the user would similarly actuate the plunger distally, either by twisting and/or pushing the handle to create pressure within reagents chamber. As before, the pressure created within the reagents chamber would break the membrane seal between the distal end of reagents chamber and the flow barrier, and when the user further pushes or twists and pushes on the handle, any liquid contained within the reagents chamber will be pushed past the venting barrier and into the capillary sampler, where the liquid will mix with the sample in the capillary sampler before being pushed onto a sample receiving area for an assay.

In some embodiments of the device, there may be markings on the outside of the sample collection and dispensing device to guide the user in dispensing the liquids from the reagents chamber and applying the sample with any liquids from the reagents chamber to the corresponding assaying device.

Figure 2:
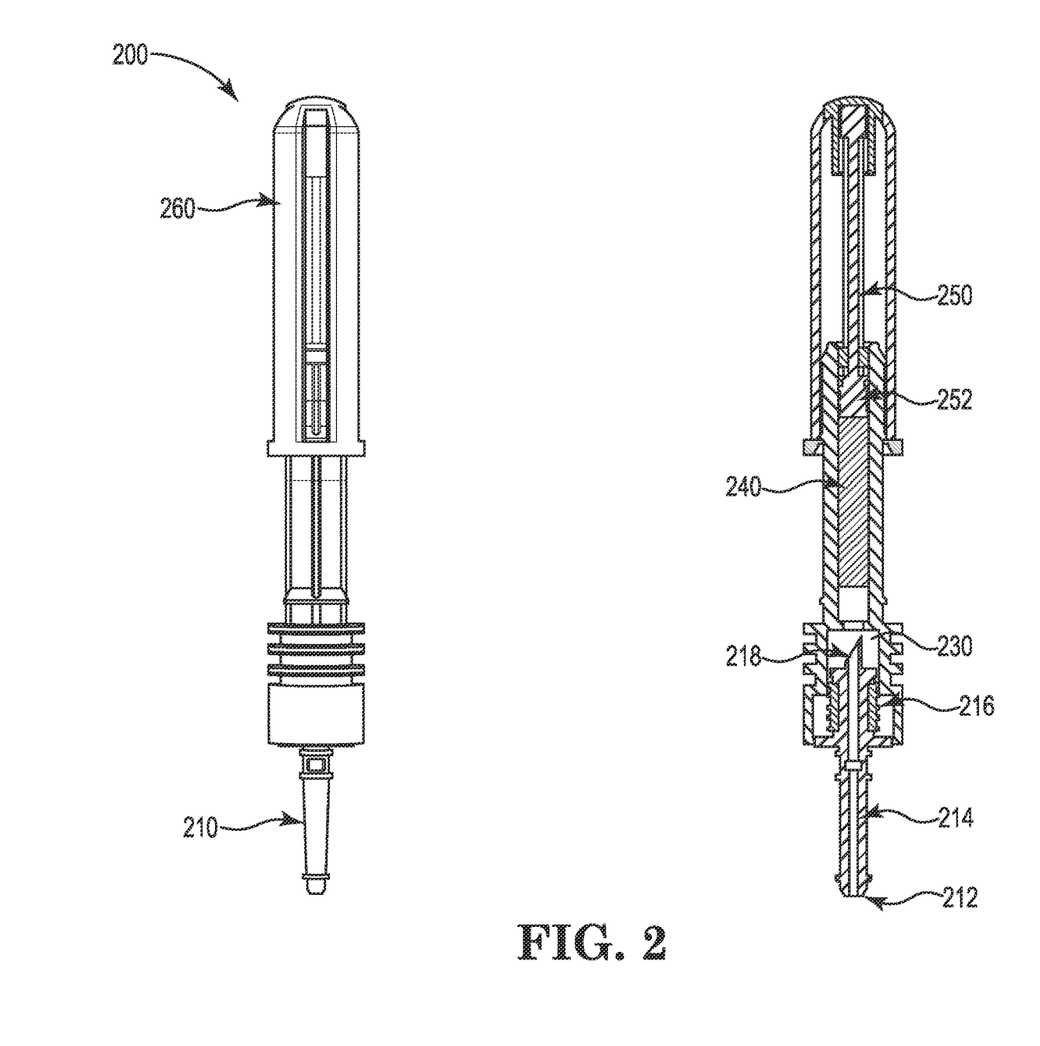
FIG. 2 further illustrates an example of a sample collection and dispensing device, consistent with the present disclosure.

Turning to FIG. 2, a second embodiment of the sample collecting and dispensing device is shown. Sample collecting and dispensing device 200 includes a capillary sampler 210 at device 200's distal end and a handle 260 at proximal end of device 200. A reagents chamber 240 is disposed between handle 260 and capillary sampler 210. A membrane 230 is disposed at the distal end of reagents chamber 240.

Continuing with FIG. 2, plunger 250 is coupled to handle 260 and where plunger 250 is configured to extend axially within reagents chamber 240 when a user actuates handle 260. Plunger 250 includes a plunger piston 252 that maintains liquid contained in reagents chamber 240. Plunger piston 252 can be coated with a rubberized material such that it makes a liquids tight seal with the internal surfaces of the reagents chamber to prevent leakage of any liquids past the plunger. For capillary sampler 210, an opening 212 and corresponding capillary 213 extends through capillary sampler 210. Capillary sampler 210 further includes an open-bore needle 218 at its proximal end that is in fluid communication with opening 212 through capillary 214. The open-bore needle can be configured to align with the distal end of the reagents chamber such that liquid following from the reagents chamber will fill and flow through the open-bore needle.

Capillary sampler 210 proximal end may mate with reagents chamber 240 distal end. Reagents chamber 240 is designed to maintain an aliquot of liquid within device 200 where one end (proximal end) of reagents chamber 240 is defined by plunger piston 252 and the second end (distal end) of reagents chamber 240 is defined by a membrane.

Capillary sampler 210 may include a series of protrusions 216 that couple to reagents chamber 240 such that when actuated, the user can "click", feel and/or hear the distal end edge of the reagents chamber 240 move past each protrusion 216 along proximal end of capillary sampler 240. The protrusions are so disposed on the capillary sampler to alert the user (through either hearing or feeling the clicks) that they have pushed the handle sufficiently to expose the membrane that maintains the liquids within the reagents chamber to the needle end of the capillary sampler allowing the needle to pierce the barrier and allowing the liquids contained within the reagents chamber to flow from the needle through the capillary to the tip of the capillary sampler where the sample is held. In some embodiments, the user twists the handle to actuate the plunger for piercing the membrane and dispensing the liquid contained within the reagents chamber. In other embodiments, the user may push the handle to actuate the plunger and plunger piston, thereby increasing the pressure within the reagents chamber for breaking the membrane and releasing the liquid maintained within the reagents chamber. In yet other embodiments, the user can use a combination of a twist and push motion on the handle to actuate the plunger and plunger rod assembly to decrease the volume of the reagents chamber and thereby creating pressure for breaking the membrane that aids in maintaining liquid within the reagents chamber.

In any embodiments of the sample collection and dispensing device disclosed, the device may include grip elements that aide with a user updating a sample, to dispensing the liquids in the reagent chamber and to the final step of attaching the sample collection and dispensing device to the assaying device.

Described herein are methods of using the different embodiments of the sample collection and dispensing device disclosed. The sample collecting and dispensing device can be used to draw up a sample from a finger prick, where the sample is blood. But it should be understood that the sample collecting and dispensing device can be used to retain other biological samples, where non-limiting examples of biological samples may be saliva, urine, and so forth. It is also contemplated that non-biological samples may be taken up by the sample collecting and dispensing device and applied to a corresponding tester. The sample is taken up using capillary action.

Figure 5:
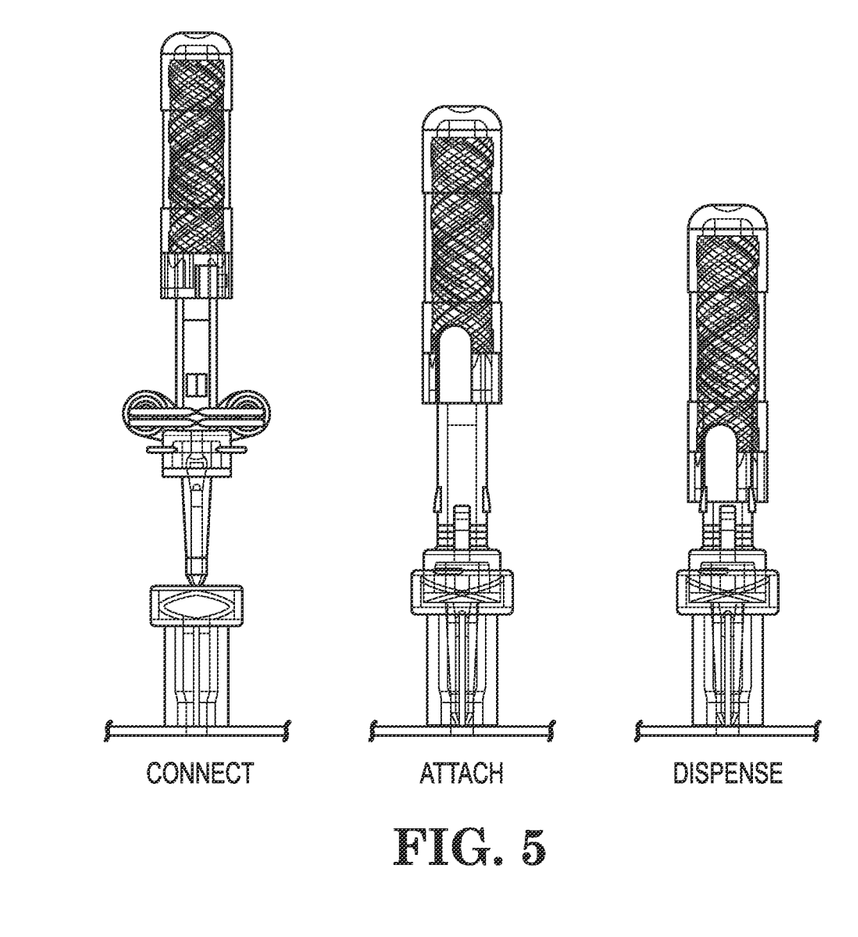
FIG. 5 illustrates an example sample collection and dispensing device and a corresponding assaying device, consistent with the present disclosure.

Once the sample is drawn into the capillary portion of the sample collecting and dispensing device, the user can attach the sample collecting and dispensing device to a corresponding tester having a receiving port. FIG. 5 shows schematic of the three step process. Once the distal end of the sample collecting and dispensing device is screwed or snapped into place into the corresponding tester, the user can twist and push the handle distally to actuate the plunger, which creates pressure within the reagents chamber. The pressure created in the reagents chamber then breaks the seal between the distal end of the reagents chamber and the flow barrier, allowing liquid contained within the reagents chamber to flow to the capillary sampler and flush the sample held there onto the test device.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present.

Although described or shown with respect to one embodiment, the features and elements described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as"/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

The term "sample", as used herein, generally refers to any material capable of being drawn up by capillary action, including for example, foods and allied products, clinical, and environmental samples. However, the sample will generally be a biological sample, which may contain any viral or cellular material, including all prokaryotic or eukaryotic cells, viruses, bacteriophages, mycoplasmas, protoplasts, and organelles. Such biological material may thus comprise all types of mammalian and non-mammalian animal cells, plant cells, algae including blue-green algae, fungi, bacteria, protozoa, etc. Representative samples thus include whole blood and blood-derived products such as plasma, serum and buffy coat, urine, feces, cerebrospinal fluid or any other body fluids, tissues, cell cultures, cell suspensions, etc.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc.

Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A sample collecting and dispensing apparatus comprising:
    a capillary sampler disposed on a first end of the sample collecting and dispensing apparatus, wherein the capillary sampler is configured to collect a fluid sample via an opening and a capillary body;
    a reagents chamber in fluid communication with the capillary sampler;
    a barrier assembly disposed between the capillary sampler and the reagents chamber, wherein the barrier assembly is configured to separate fluid in the reagents chamber from the capillary sampler;
    a plunger assembly disposed on a second end of the sample collecting and dispensing apparatus. the second end being opposite the first end, wherein the plunger assembly is configured to modify the barrier assembly to dispense the fluid from the reagents chamber to the capillary sampler responsive to application of a force in the direction of the first end;
    a venting barrier disposed in the capillary body; and
    a liquid barrier including a deformable ball configured to displace into a cavity of the capillary body in response to pressure within the reagents chamber being at or above a threshold level of pressure,
    wherein the venting barrier is configured to prevent the deformable ball of the liquid barrier from passing beyond the cavity of the capillary body and to permit passage of the fluid from the reagents chamber into the capillary sampler.

2. The sample collecting and dispensing apparatus of claim 1, wherein an internal surface of the capillary body and an internal surface of the opening of the capillary sampler are coated with a hydrophilic material.

3. The sample collecting and dispensing apparatus of claim 1, wherein the venting barrier includes sintered polyethylene grains.

4. The sample collecting and dispensing apparatus of claim 1, wherein the liquid barrier is configured to:
    maintain the fluid in the reagents chamber in response to pressure within the reagents chamber being below a threshold level of pressure; and
    permit passage of fluid from the reagents chamber to the capillary sampler in response to pressure within the reagents chamber being at or above the threshold level of pressure.

5. The sample collecting and dispensing apparatus of claim 1, wherein the barrier assembly further includes:
    the venting barrier;
    the liquid barrier including the deformable ball; and
    a pedestal disposed in the capillary body and configured to prevent the deformable ball of the liquid barrier from passing beyond a particular point within the capillary body and to permit passage of the fluid from the reagents chamber into the capillary sampler.

6. The sample collecting and dispensing apparatus of claim 1, wherein the venting barrier is disposed in the capillary body and in a venting aperture defined by a side wall of the capillary body.

7. The sample collecting and dispensing apparatus of claim 6, wherein the venting barrier is configured to:
    limit a volume of the fluid sample collected in the capillary body in response to pressure within the reagents chamber being below a threshold level of pressure; and
    permit passage of fluid from the reagents chamber to the capillary sampler in response to pressure within the reagents chamber being at or above the threshold level of pressure.

8. The sample collecting and dispensing apparatus of claim 6, wherein the venting barrier is configured to permit air to exit the capillary body via the venting aperture in the side wall of the capillary body responsive to collection of the fluid sample via the opening.

9. A sample collecting and dispensing apparatus comprising: a capillary sampler disposed on a first end of the sample collecting and dispensing apparatus, wherein the capillary sampler is configured to collect and dispense a fluid sample via an opening and a capillary body;
    a reagents chamber storing a fluid reagent specific to the fluid sample to be collected, wherein the reagents chamber includes a reagents chamber distal end attached to and in fluid communication with the capillary sampler and a reagents chamber proximal end;
    a liquid barrier disposed on the reagents chamber distal end configured to prevent the fluid reagent from passing from the reagents chamber to the capillary sampler under atmospheric pressures; and
    a plunger assembly including a handle and a plunger rod disposed on a second end of the sample collecting and dispensing apparatus, wherein the plunger assembly is adjacently connected to the reagents chamber proximal end through mated threads, and wherein the plunger rod is configured to translate distally along the reagents chamber to decrease a volume of the fluid reagent in the reagents chamber and permit the fluid reagent to release from the reagents chamber,
    wherein the reagents chamber further includes mating features disposed on an external surface of the reagents chamber and configured to translate distally along mated threads disposed on an inside surface of the handle.

10. The sample collecting and dispensing apparatus of claim 9, wherein the liquid barrier includes an elastomeric cord.

11. The sample collecting and dispensing apparatus of claim 9, wherein the handle further includes an indicator configured to provide a visual indication in response to the volume of the fluid reagent in the reagents chamber being fully dispensed.

12. The sample collecting and dispensing apparatus of claim 9, wherein the handle of the plunger assembly further includes mating features disposed on an internal surface of the handle and configured to translate distally along mated threads disposed on an external surface of the reagents chamber.

13. The sample collecting and dispensing apparatus of claim 9, wherein the capillary sampler is configured to dispense the fluid sample and the fluid reagent to a corresponding test device responsive to translation of the plunger rod distally along the reagents chamber.

14. The sample collecting and dispensing apparatus of claim 9, further including coupling features disposed on an exterior surface of the apparatus for coupling the apparatus to a corresponding test device.

15. The sample collecting and dispensing apparatus of claim 14, wherein the coupling features are configured to lock in a fixed position responsive to coupling of the apparatus to the corresponding test device.

16. A method of sample collecting and dispensing, comprising:
    collecting a fluid sample by capillary force through an opening in a capillary sampler disposed on a first end of a sample collecting and dispensing apparatus, wherein a volume of the fluid sample is limited by a barrier assembly disposed within the capillary sampler;
    coupling the sample collecting and dispensing apparatus to a receiving port of a corresponding testing apparatus;
    responsive to application of a force on a plunger assembly disposed on a second end of the sample collecting and dispensing apparatus opposite the first end of the sample collecting and dispensing apparatus, modifying the barrier assembly to dispense fluid from a reagents chamber in fluid communication with the capillary sampler, and dispensing the fluid from the reagents chamber and the fluid sample from the as opening in a capillary sampler, and
    modifying the barrier assembly by increasing pressure in the reagents chamber and dislodging a deformable ball from a location proximal to the capillary sampler.

* * * * *